(12) United States Patent
Tanaka

(10) Patent No.: US 7,187,981 B2
(45) Date of Patent: Mar. 6, 2007

(54) IMPLANTABLE ELECTRODE LEAD

(75) Inventor: Tetsuo Tanaka, Tokyo (JP)

(73) Assignee: Terumo Kabushiki Kaisha, Tokyo (JP)

(*) Notice: Subject to any disclaimer, the term of this patent is extended or adjusted under 35 U.S.C. 154(b) by 334 days.

(21) Appl. No.: 10/915,456

(22) Filed: Aug. 11, 2004

(65) Prior Publication Data
US 2005/0060015 A1 Mar. 17, 2005

(30) Foreign Application Priority Data
Aug. 12, 2003 (JP) ............... 2003-292247

(51) Int. Cl.
*A61N 1/05* (2006.01)

(52) U.S. Cl. .................... 607/125; 607/128

(58) Field of Classification Search ........ 607/116–132, 607/72, 73, 74, 75; 600/375
See application file for complete search history.

(56) References Cited

U.S. PATENT DOCUMENTS

| | | | |
|---|---|---|---|
| 4,573,481 A | 3/1986 | Bullara | |
| 4,608,985 A | 9/1986 | Crish et al. | |
| 4,628,942 A | 12/1986 | Sweeney et al. | |
| 5,433,744 A * | 7/1995 | Breyen et al. | 607/125 |
| 5,755,750 A * | 5/1998 | Petruska et al. | 607/75 |
| 6,999,819 B2 * | 2/2006 | Swoyer et al. | 607/117 |

FOREIGN PATENT DOCUMENTS

JP 8-10338 1/1996

* cited by examiner

*Primary Examiner*—Robert E Pezzuto
(74) *Attorney, Agent, or Firm*—Buchanan Ingersoll & Rooney PC

(57) ABSTRACT

An implantable electrode lead including: a distal portion having at least one electrode; a proximal portion having a connector for connection to an implantable stimulation generator includes a power source for the electrode and is disposed in a living body; and a conductor portion which is connected to the distal portion and the proximal portion and is composed of an electrical conductor for transmission of electrical signals and an insulator covering the outside of the electrical conductor, and a fixation portion having a tip end and a base end for disposing over a part of the conductor portion, wherein a lubricant coating layer is provided on a part of the surface of the conductor portion, and the lubricant coating layer is absent on the conductor portion surface ranging at least from the portion disposed at the base end of the fixation portion to the portion provided with the electrode, of the surface of the conductor portion.

10 Claims, 4 Drawing Sheets

IMPLANTABLE ELECTRODE LEAD

BACKGROUND OF THE INVENTION

An apparatus which is implanted in a living body to generate an electrical stimulus for therapeutic purpose, such as a nerve stimulator and a muscle stimulator, is composed of an implantable stimulation generator serving as a power source portion and an implantable electrode lead including an electrode and a lead. The present invention relates to an implantable electrode lead, and particularly to an implantable lead which includes a lubricant coating layer on a specified portion thereof and in which operability at the time of implanting is improved and the inflammation and the patient's feeling of physical disorder generated after the implanting are lessened.

Conventionally, there have been used cardiac pacemakers, defibrillators, nerve stimulators, pain alleviators, epilepsy treating apparatus, electric muscle stimulators and the like, which are apparatus for conducting treatment by giving an electrical stimulus directly or indirectly to the heart, nerve, brain, muscle or the like. These apparatus are each composed of an implantable stimulation generator having a power source and generating an electrical stimulus, and an implantable electrode lead for transmitting the generated electrical stimulus to the site on which the stimulus is to act.

Particularly, the nerve stimulator, pain alleviator, epilepsy treating apparatus, and muscle stimulator are apparatus for conducting treatment by giving an electrical stimulus directly to the nerve, brain or muscle, and in each of the apparatus it is necessary to cause the electrode lead to indwell in the living body for the purpose of giving a target site the electrical stimulus generated by the implantable stimulation generator. For this reason, the implantable electrode lead in each of the apparatus is composed of:

At least one electrode for giving an electrical stimulus to the nerve, brain, muscle or the like;

A connector for electrical connection to the implantable stimulation generator of the nerve stimulator, pain alleviator, epilepsy treating apparatus, muscle stimulator or the like; and A conductor portion composed of an electrical conductor and an insulator covering the outside of the electrical conductor.

Incidentally, an implantable electrode lead to be used in a subcutaneous manner has a structure in which the electrode is connected to the nerve, brain, muscle or the like, most part of the conductor portion is inserted under the subcutaneous tissue, and the conductor portions thus inserted under the subcutaneous tissue is connected to the implantable stimulation generator of the nerve stimulator, pain alleviator, epilepsy treating apparatus, muscle stimulator or the like through a connector. The subcutaneous tissue herein means a tissue located between the skin and a muscle.

Now, one example of the conventional implantable electrode lead will be described below.

The implantable electrode lead is composed of a proximal portion having a connector for connection to the implantable stimulation generator of the nerve stimulator or the like, a distal portion having an electrode set in contact with the target site so as to give an electrical stimulus to the target site, a conductor portion connected to the proximal portion and the distal portion so as to transmit the electrical stimulus, and a fixation portion provided on a part of the outside surface of the conductor portion so as to fix the implantable electrode lead in the living body.

At the time of implanting, the electrode of the implantable electrode lead is connected to the target site of the nerve, brain, muscle or the like, and the fixation portion is fixed to the living body, whereby the electrode is prevented from moving. Further, the connector is laid under the subcutaneous tissue and connected to the implantable stimulation generator. In mounting the implantable electrode lead, the implantable stimulation generator is in many cases disposed remote from the electrode, and the proximal portion is in some cases moved to the implantable stimulation generator by passing it under the subcutaneous tissue over a long distance. In many case, however, the insulator on the implantable electrode lead is formed of a silicone, which is a polymer high in bio-stability and durability, and the silicone has a comparatively high coefficient of dynamic friction in relation to the subcutaneous tissue, so that it is difficult to pass the implantable electrode lead under the subcutaneous tissue.

On the other hand, for the purpose of facilitating the passage of the implantable electrode lead under the subcutaneous tissue, it is in some cases practiced to preliminarily insert a subcutaneous tunneling tool under the subcutaneous tissue and to pass the implantable electrode lead through the inside of a lumen of the subcutaneous tunneling tool. However, since the silicone used for forming the insulator on the conductor portion of the implantable electrode lead generates a high frictional force on the inside wall of the lumen, the performance of passage of the implantable electrode lead in the lumen is low, so that it is difficult to smoothly pass the proximal portion under the subcutaneous tissue, even by use of the subcutaneous tunneling tool.

An electrode lead for a cardiac pacemaker in which the surface of a conductor portion is coated with a hydrophilic polymer for reducing the frictional force on the surface of a silicone-made electrode lead and thereby promising an easier sliding of the electrode lead has been disclosed (see Japanese Patent Laid-open No. Hei 8-10338). In the electrode lead described in Japanese Patent Laid-open No. Hei 8-10338, however, the conductor portion is coated with the hydrophilic polymer up to the tip end of the electrode lead, and the publication does not include a description that the electrode lead includes a fixation portion. Therefore, it is difficult to stably fix the implantable electrode lead in a comparatively broad space, although it may be possible to stably fix the electrode lead in a narrow place such as in a blood vessel. Even in the case where the implantable electrode lead has a fixation portion, the structure in which the conductor portion is entirely coated with the hydrophilic polymer results in that the surface of the conductor portion is slippery and it is impossible to stably fix the implantable electrode lead in a living body.

SUMMARY OF THE INVENTION

It is an object of the present invention to provide an implantable electrode lead in which operability can be enhanced by reducing the frictional force generated between a conductor portion and the subcutaneous tissue, muscle or the inside wall of the lumen of a subcutaneous tunneling tool or the like at the time of installing the implantable electrode lead into a living body or withdrawing the implantable electrode lead therefrom and in which an electrode can be assuredly fixed in the body tissue after the installation.

It is another object of the present invention to lessen the inflammation reaction generated due to the implanting of an implantable electrode lead into a living body and to reduce the burden exerted on the patient.

As a result of extensive and intensive studies for obtaining an implantable electrode lead suitable for solving the above-mentioned problems, the present inventors have found out that, where a lubricant coating layer is provided on a conductor portion over a specified distance starting at the proximal end of an implantable electrode lead to be used with an implantable stimulation generator and the lubricant coating layer is absent over a specified distance starting at the distal end of the implantable electrode lead, it is possible to reduce the frictional force generated between the conductor portion and the subcutaneous tissue, muscle or the inside wall of the lumen of a subcutaneous tunneling tool or the like at the time of installing the implantable electrode lead into a living body or withdrawing the implantable electrode lead therefrom and, further, to assuredly fix an electrode in a target site after the installation. Based on the finding, the present invention has been completed. Furthermore, the present inventors have invented an implantable electrode lead which contains a steroid-based antiphlogistic as required and in which a lubricant coating layer with high biocompatibility is provided on the outside of a conductor portion, whereby it is possible to lessen the inflammation reaction generated due to the implanting of the implantable electrode lead into the living body and to reduce the burden exerted on the patient.

In accordance with one aspect of the present invention, there is provided an implantable electrode lead including:

a distal portion having at least one electrode;

a proximal portion having a connector for connection to an implantable stimulator which is disposed in a living body and includes a power source for the electrode; and a conductor portion which is connected to the distal portion and the proximal portion and is composed of an electrical conductor for transmission of electrical signals and an insulator covering the outside of the electrical conductor, and a fixation portion having a tip end and a base end for disposing over a portion of the conductor portion, wherein a lubricant coating layer is provided on a part of the surface of the conductor portion, and the lubricant coating layer is absent on the conductor portion surface ranging at least from the portion disposed at the base end of the fixation portion to the portion provided with the electrode, of the surface of the conductor portion.

In accordance with another aspect of the present invention, there is provided an implantable electrode lead including:

a distal portion having at least one electrode;

a proximal portion having a connector for connection to an implantable stimulator which includes a power source for the electrode and is disposed in a living body; and a conductor portion which is connected to the distal portion and the proximal portion and is composed of an electrical conductor for transmission of electrical signals and an insulator covering the outside of the electrical conductor, wherein a lubricant coating layer is provided on the surface of the conductor portion over a distance of not less than 100 mm in the distal direction starting at the connector, and the lubricant coating layer is absent on the surface of the conductor portion over a distance of not less than 30 mm in the proximal direction starting at the electrode.

In the implantable electrode lead as above, the material constituting the lubricant coating layer is preferably a hydrophilic polymeric material which develops lubricity when wetted.

The hydrophilic polymeric material is preferably polyvinyl pyrrolidone (PVP) or an acrylic acid-based polymer.

The hydrophilic polymeric material may further contain a steroid-based antiphlogistic or be covalent-bonded to a steroid-based antiphlogistic.

In the implantable electrode lead as above, the components preferably have such sizes that the electrode can be disposed at a cervical nerve of the living body and the connector can be disposed in the chest region of the living body, at the time of implanting.

Incidentally, the cervical nerve herein means the vagus nerve or sympathetic nerve.

In the implantable electrode lead according to the present invention, the lubricant coating layer is provided on the conductor portion over a specified distance starting at the proximal end of the implantable electrode lead, and the lubricant coating layer is absent on the conductor portion over a specified distance starting at the distal end of the implantable electrode lead. This structure makes it possible to reduce the frictional force generated between the conductor portion and the subcutaneous tissue, muscle or the inside wall of the lumen of a subcutaneous tunneling tool or the like at the time of installing the implantable electrode lead into the living body or withdrawing the implantable electrode lead therefrom, to thereby obtain a high operability, and further to assuredly fix the electrode in the body tissue after the installation. Furthermore, where a lubricant coating layer containing a steroid-based antiphlogistic as required and being high in biocompatibility is provided on the outside of the conductor portion, it is possible to lessen the inflammation reaction generated due to the implanting of the implantable electrode lead into the living body and to reduce the burden exerted on the patient.

BRIEF DESCRIPTION OF THE DRAWINGS

The above and other objects, features and advantages of the present invention will become apparent from the following description and appended claims, taken in conjunction with the accompanying drawings, in which:

DESCRIPTION OF THE PREFERRED EMBODIMENT

Now, the implantable electrode lead according to the preferred embodiment will be described in detail below, referring to FIG. 1.

Figure 1:
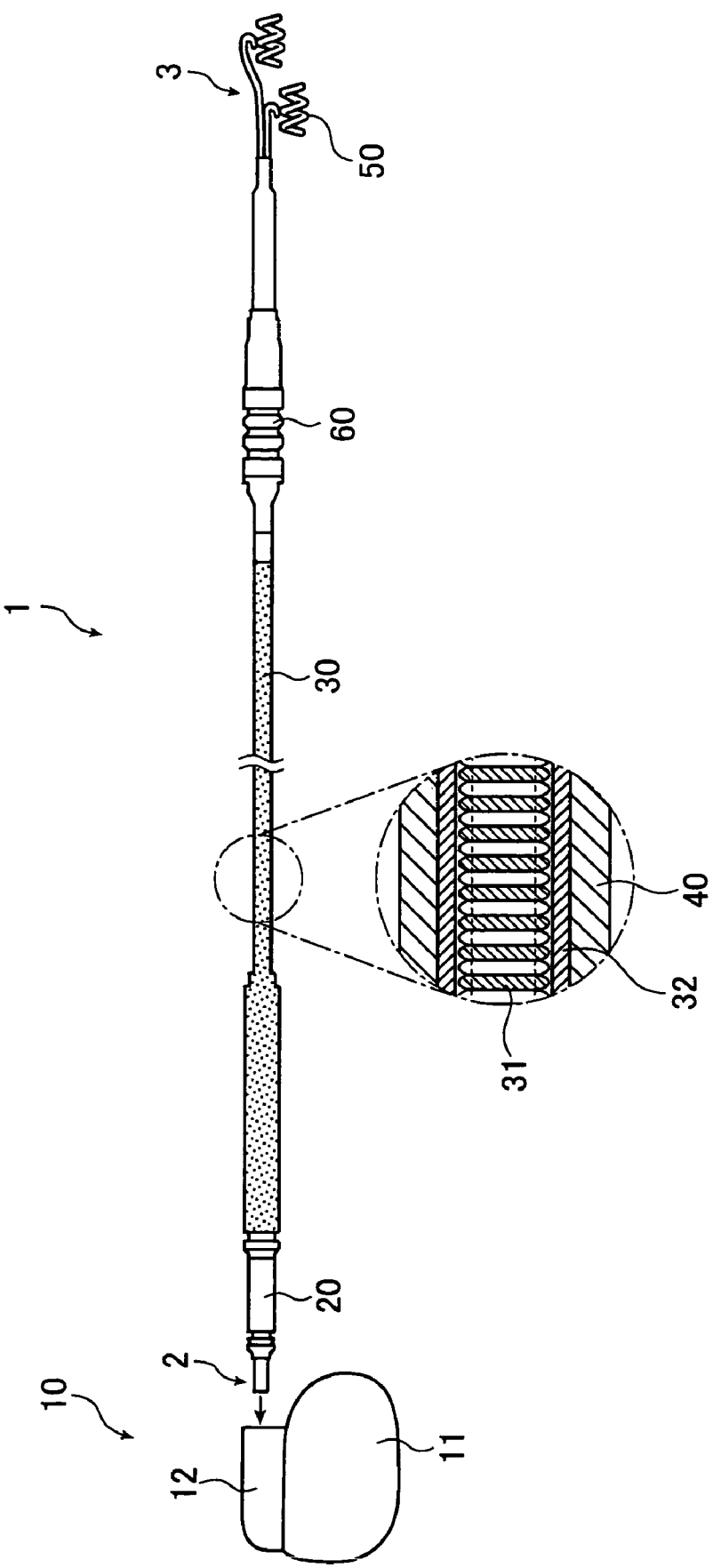
FIG. 1 is a schematic view of one example of the implantable electrode lead according to the preferred embodiment and an implantable stimulation generator.

FIG. 1 is a schematic illustration of one example of the implantable electrode lead according to the preferred embodiment and an implantable stimulation generator.

The implantable electrode lead 1 according to a first embodiment of the present invention is an implantable electrode lead comprising a distal portion 3 having at least one electrode 50, a proximal portion 2 having a connector 20 for connection to an implantable stimulation generator 10 which comprises a power source for the electrode 50 and is disposed in a living body, a conductor portion 30 which is connected to the distal portion 3 and the proximal portion 2 and is composed of an electrical conductor 31 for transmission of electrical signals and an insulator 32 covering the outside of the electrical conductor 31, and a fixation portion 60 having a tip portion and a base portion for disposing over a part of the conductor portion 30, wherein A lubricant coating layer 40 is provided on a part of the surface of the conductor portion 30, and the lubricant coating layer 40 is absent on the surface of the conductor portion 30 in the area ranging at least from the portion disposed at the base end of the fixation portion 60 to the portion provided with the electrode 50, of the surface of the conductor portion 30.

As an implantable stimulation generator 10 to be used in connection with the implantable electrode lead 1, there can be used any of those conventionally used in cardiac pacemakers, defibrillators, nerve stimulators, pain alleviators, epilepsy treating apparatus, muscle stimulators and the like. Each of these implantable stimulation generators 10 is generally composed of a case 11 (can) in which a power source (battery) and an electronic circuit for driving the electrode 50 are sealed, and a connector housing 12 incorporating therein connectors for electrical and mechanical connection and fixation to the electrode lead 1.

The implantable stimulation generator 10 is generally circular, elliptic or rectangular in shape, and is sized to be suitable for implanting. The implantable stimulation generator 10 is generally implanted into a pocket formed beneath the skin of the left chest region of the patient by the surgeon, and the back (or face) surface of the implantable stimulation generator is in contact with the chest muscle; however, the implantable stimulation generator 10 may not necessarily be implanted in the left chest region.

In the embodiment, as the electrode 50, the connector 20, the conductor portion 30, and the fixation portion 60 belonging to the implantable electrode lead 1, there can be used those which have conventionally been known.

The number of the electrode(s) 50 used in the embodiment is at least one. For example, two electrodes may be used, one being an indifferent electrode and the other a different electrode. The indifferent electrode is electrically connected to the implantable stimulation generator 10, and is composed, for example, of a stainless steel wire of which a tip end portion is embedded in the body tissue. On the other hand, the different electrode is paired with the indifferent electrode, to function as an exciting electrode for stimulating the living body.

A coil form electrode, which is preferably used in the embodiment, has a structure in which an electrode terminal is exposed on the inside of the coil, so that the electrode terminal can be fixed in close contact with a target site by winding the coil around the target site. Thus, the electrode terminal has both the function of giving a stimulus to the target site and the function of fixing the electrode itself to the target site. In general, two such electrodes are used to form a pair, and the electrodes have positive and negative potentials, respectively. As such an electrode, for example, a bipolar exciting electrode of the type described in U.S. Pat. No. 4,573,481 is used. The electrode which itself has the function of fixing the electrode terminal in close contact with the target site is not limited to the above-mentioned coil form electrode, and a variety of electrodes can be used as the electrode. Examples of the electrodes usable include the cuff electrodes described in U.S. Pat. Nos. 4,608,985 and 4,628,942, and the hook electrode described in U.S. Pat. No. 5,755,750.

Furthermore, where the electrode 50 having the function of fixing the electrode itself to the target site is used in combination with the fixation portion 60 which will be described later, the electrode 50 can be fixed to the target site more assuredly, which is preferable.

The conductor portion 30 is connected to both the electrode 50 and the connector 20, and is composed of the electrical conductor 31 for transmission of electrical signals and an insulator 32 covering the outside of the electrical conductor 31.

Where there are at least two electrodes 50, the conductor portion 30 may be so configured that at least two electrical conductors 31 connected respectively to the electrodes are set insulated from each other and the outside of each of the electrical conductors 31 is covered with the insulator 32.

For forming the insulator 32, polymeric materials can be used favorably. Preferred examples of the polymeric materials include silicones, fluorosilicones, fluoroelastomers, and polyurethane. Among these examples, particularly preferred are silicones, in view of their excellent chemical stability in long-time implanting in the living body and easy provision of the lubricant coating layer 40.

The fixation portion 60 comprises a tip end and a base end for disposing over a part of the conductor portion 30, and fixes the implantable electrode lead 1 to the living body. The fixation portion 60, generally, is tubular in shape; however, the shape of the fixation portion 60 is not particularly limited, as long as the tip end and the base end thereof can be disposed over a part of the conductor portion 30 and the fixation portion 60 comprises a means for fixing the implantable electrode lead 1 to the living body. In addition, it suffices that at least one fixation portion 60 is provided.

The fixation portion 60 is a device for stably fixing the implantable electrode lead 1 in the living body by being fixed to the body tissue through suture or the like. This ensures that the electrode 50 is prevented from moving from the target site when the conductor portion 30 is pulled in the direction of the proximal portion 2, for example.

The fixation portion 60 may be movable along the outside surface of the conductor portion 30 in the stage before the installation in the living body. The operator can move the fixation portion 60 to a favorable position, taking into account the positional relationship between the nerve to which the electrode 50 is to be fixed and the subcutaneous tissue to which the fixation portion 60 is to be fixed by suture or the like. The fixation portion 60 is preferably immovable on the conductor portion 30 after the installation in the living body. Specifically, for example, the fixation portion 60 is designed to be immovable on the conductor portion 30 because it is fixed through co-fastening it with the subcutaneous tissue by a suture. In order that the fixation portion 60 would not move by sliding on the conductor portion 30, therefore, it is desirable not to provide the lubricant coating layer in the range in which the fixation portion 60 can be finally disposed.

The whole length of the fixation portion 60 is 15 to 30 mm.

To be more specific, for example, as the fixation portion 60, there can be used a sutural sleeve which is a tubular body capable of being disposed over part of the conductor portion 30 and provided in its outer peripheral surface with a groove for fitting the thread for fixing the fixation portion 60 through suturing the fixation portion 60 with the living body and which is movable along the outside surface of the conductor portion 30. Where the sutural sleeve is provided, it is possible to fix the sutural sleeve after moving the sutural sleeve to an appropriate position and to regulate the distance between the electrode 50 and the sutural sleeve, i.e., the play of the conductor portion 30, at the time of installing the implantable electrode lead 1 into the living body. In addition, since the implantable electrode lead 1 can be fixed in the living body through the sutural sleeve, it is possible to prevent the electrode 50 from moving and, further, to avoid damage to the conductor portion 30 due to direct ligation of the conductor portion 30, which is preferable.

The connector 20 is located at the proximal portion 2 of the implantable electrode lead 1, and is electrically and mechanically connected to a connector incorporated in the connector housing 12 of the implantable stimulation generator 10. As a result, the electrode 50 located at the distal portion 3 of the implantable electrode lead 1 is electrically connected to the implantable stimulation generator 10 through the conductor portion 30. As the connector, conventional kinds of connector such as male type connectors and female type connectors can be used, as long as they correspond to the connector incorporated in the connector housing 12.

Next, the lubricant coating layer 40 in the embodiment will be described in detail.

The lubricant coating layer 40 is provided on a part of the surface of the conductor portion 30. It should be noted here that the lubricant coating layer 40 is absent on the surface of the conductor 30 in the area ranging at least from the portion disposed at the base end of the fixation portion 60 to the portion provided with the electrode 50, of the surface of the conductor portion 30.

With the lubricant coating layer 40 provided at such a position, it is possible to reduce the frictional force generated between the conductor portion 30 and the subcutaneous tissue, muscle or the inside wall of the lumen of the subcutaneous funneling tool or the like at the time of installing the implantable electrode lead 1 into the living body or withdrawing the implantable electrode lead 1 therefrom. Further, since at least the portion ranging from the base end of the fixation portion 60 to the electrode 50, of the surface of the conductor portion 30, is not provided thereon with the lubricant coating layer 40, even a movable fixation portion 60 such as the above-mentioned sutural sleeve would not slide on the surface of the conductor portion 30 and the electrode 50 can be assuredly fixed to the living body, as compared with the case where the portion is provided thereon with the lubricant coating layer 40. In addition, even in the case where the fixation portion 60 is fixed to the conductor portion 30 previously, the absence of the lubricant coating layer on the surface of the fixation portion 60 ensures that the fixation portion 60 would not slide at the location where it is bound to the body tissue and that the electrode 50 can be assuredly fixed to the living body.

The lubricant coating layer 40 is preferably formed of a hydrophilic polymeric material such as plant- and animal-derived natural water-soluble polymers, semi-synthetic water-soluble polymers, and synthetic water-soluble polymers. Further, the water-soluble polymers are desirably turned to be water-insoluble by such means as crosslinking. Specific examples of the hydrophilic polymeric material include polyvinyl pyrrolidone (PVP), acrylic acid-based polymers, polyvinyl alcohols, polyethylene glycol, cellulose derivatives such as cellulose, methyl cellulose, and hydroxypropyl cellulose; sugars such as mannan, chitosan, guar gum, xanthan gum, gum arabic, glucose, and sucrose; amino acids and the derivatives thereof such as glycine, serine, and gelatin; and natural polymers such as polylactic acid, sodium alginate, and casein. In the embodiment, PVP or an acrylic acid-based polymer is preferably used, in view of excellent compatibility with the insulator 32 and excellent operability at the time of installing or withdrawing the implantable electrode lead.

Furthermore, where the implantable electrode lead comprises the lubricant coating layer in which the hydrophilic polymeric material contains a steroid-based antiphlogistic such as dexamethasone sulfate, methylprednisolone, prednisolone, betamethazone, triamcinolone, paramethasone, fluocinolone acetonide, and beclomethasone, or is covalent-bonded to a steroid-based antiphlogistic, it is possible to lessen the inflammation reaction generated when the implantable electrode lead is installed in the living body, particularly under the subcutaneous tissue, and to reduce the burden exerted on the patient, which is preferable.

The implantable electrode lead according to a second embodiment is an implantable electrode lead comprising a distal portion having at least one electrode, a proximal portion having a connector for connection to an implatable stimulation generator which comprises a power source for the electrode and is disposed in a living body, and a conductor portion which is connected to the distal portion and the proximal portion and is composed of an electrical conductor for transmission of electrical signals and an insulator covering the outside of the electrical conductor.

A lubricant coating layer is provided on the surface of the conductor portion over a distance of not less than 100 mm in the distal direction starting at the connector, and the lubricant coating layer is absent on the surface of the conductor portion over a distance of not less than 30 mm in the proximal direction starting at the electrode.

As the electrode, the conductor portion, the connector, and the fixation portion according to the second embodiment, the same components as those described in the first embodiment above can be used.

As the lubricant coating layer, the same as that described in the first embodiment may be used, it being desirable that the lubricant coating layer be provided on the surface of the conductor portion over a distance of not less than 100 mm in the distal direction starting at the connector and that the lubricant coating layer be absent on the surface of the conductor portion over a distance of not less than 30 mm starting at the electrode. Here, the whole length of the implantable electrode lead is preferably 400 to 500 mm. It is preferable that the lubricant coating layer is provided over a distance of not less than 200 mm, more preferably not less than 250 mm, from the connector. Besides, it is preferable that the lubricant coating layer is absent over a distance of not less than 100 mm, more preferably not less than 150 mm, from the electrode.

With the lubricant coating layer provided at such a position, it is possible to reduce the frictional force generated between the conductor portion and the subcutaneous tissue, muscle or the like and, hence, to enhance operability, at the time of installing the implantable electrode lead into the living body or withdrawing the implantable electrode lead therefrom. Similarly, also in the case of using a subcutaneous tunneling tool called tunneler for the purpose of facilitating the insertion of the implantable electrode lead into the living body, it is possible to reduce the frictional force generated between the conductor portion and the inside wall of the lumen of the subcutaneous tunneling tool and, hence, to enhance operability.

Furthermore, since the fixation portion, the electrode and the conductor portion therebetween are not provided thereon with the lubricant coating layer, the fixation portion would not slide on the surface of the conductor portion, and the electrode can be assuredly fixed in the living body.

The implantable electrode lead 1 is desirably manufactured by a method in which the lubricant coating layer 40 is preliminarily provided on a predetermined portion on the surface of the conductor portion 30, and thereafter the electrode 50, the fixation portion 60, and the connector 20 are attached in position.

The lubricant coating layer 40 can be provided by a method of applying a liquid containing the above-mentioned hydrophilic polymer dispersed in an organic solvent, a method of immersing in the liquid, or the like method. Where the insulator 32 is formed of a silicone, it is difficult for the silicone to be chemically bonded to the hydrophilic polymer and, therefore, the formation of the lubricant coating layer 40 is carried out by the following method (1) or (2).

(1) A lubricant polymer is fixed to the silicone, used as a base material, by plasma-initiated graft polymerization.

(2) A coupling compound is introduced into the silicone, used as a base material, by plasma-initiated graft polymerization, whereby the coupling compound and the lubricant polymer are brought into reaction, to develop lubricity. Here, the coupling compound has at least one photo-reactive group for photo-fixation of the coupling compound to the silicone constituting the insulator 32, and a photo-reactive group or thermo-reactive group for a photochemical reaction or thermochemical reaction between the coupling compound and the lubricant polymer. Alternatively, it is preferable that the coupling compound has a thermochemical group for thermochemically covalently adhering the coupling compound to the silicone of the insulator 32, and a photo-reactive group for photo-fixation of the coupling compound to the lubricant polymer.

Thus, the polymeric material used for forming the lubricant coating layer 40 is not limited to PVP or the acrylic acid-based polymer but may be any polymer, as long as the lubricant polymer is fixed; the polymeric material may be a maleic acid-based polymer such as maleic anhydride, or gelatin or the like.

Now, the procedure for installing the implantable electrode lead 1 into the living body will be described below by way of an example of installing the electrode 50 around the vagus nerve located in the cervical region, referring to FIGS. 2 to 5.

Figure 2:
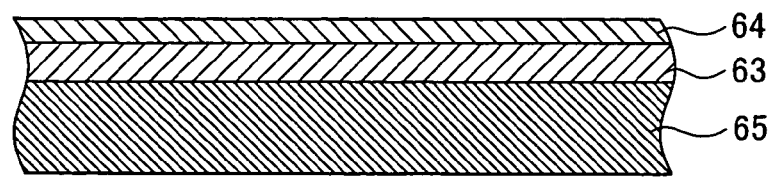
FIG. 2 is a general sectional view showing the vicinity of the surface of a skin.

FIG. 2 is a general sectional view showing the vicinity of the surface of a skin. Generally, in the vicinity of the surface of the skin of a human body, the skin 64, a subcutaneous tissue 63, and a muscle 65 are layered in this order from the skin surface.

Figure 3:
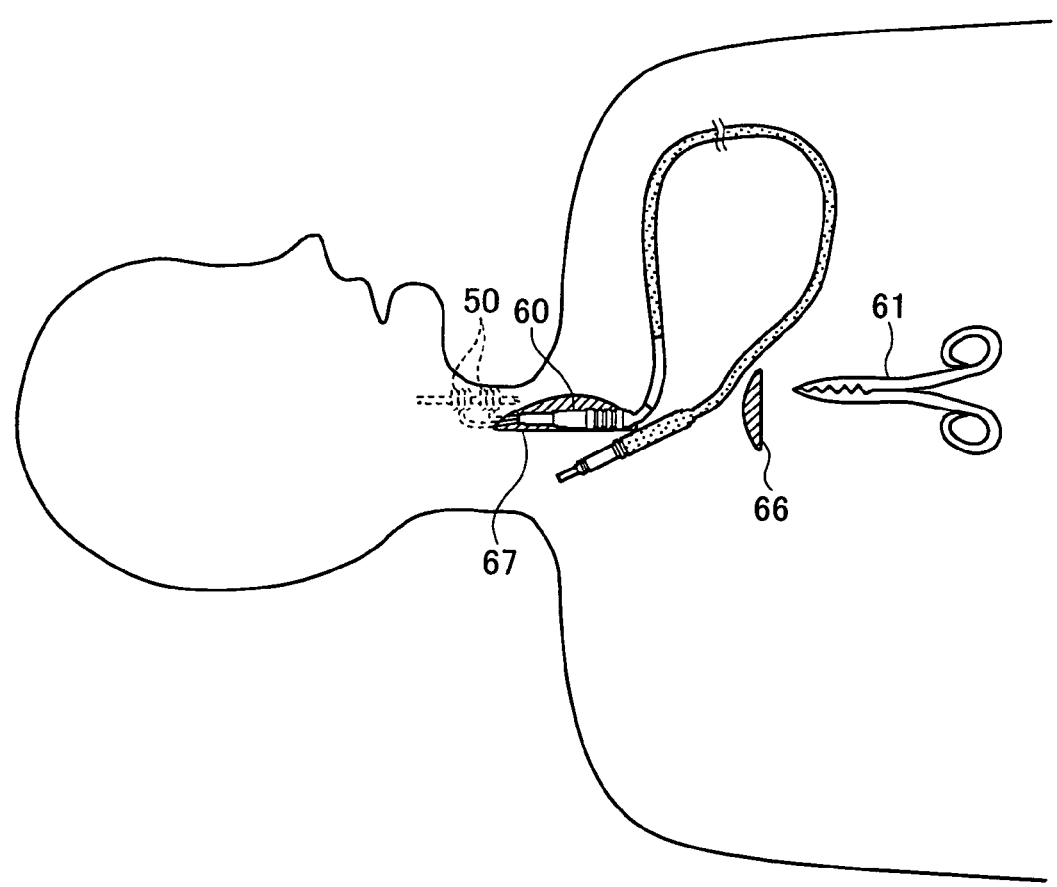
FIG. 3 is a general view showing the condition before the implantable electrode lead 1 is passed through a subcutaneous tunnel 62.
Figure 4:
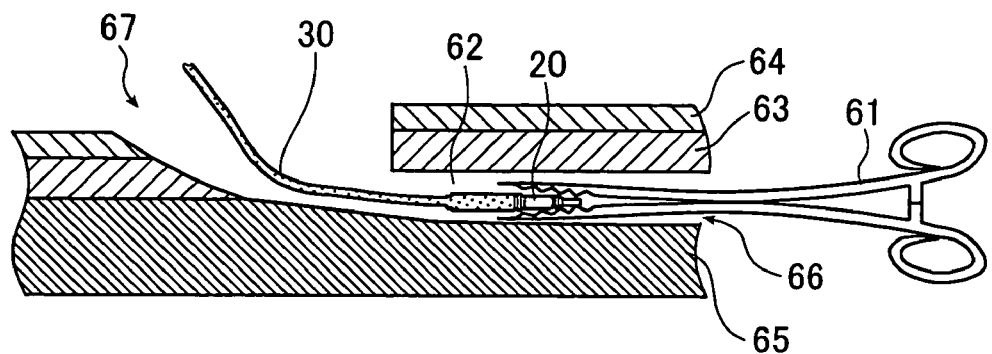
FIG. 4 is a general sectional view illustrating the manner in which the implantable electrode lead 1 is passed through the subcutaneous tunnel 62.
Figure 5:
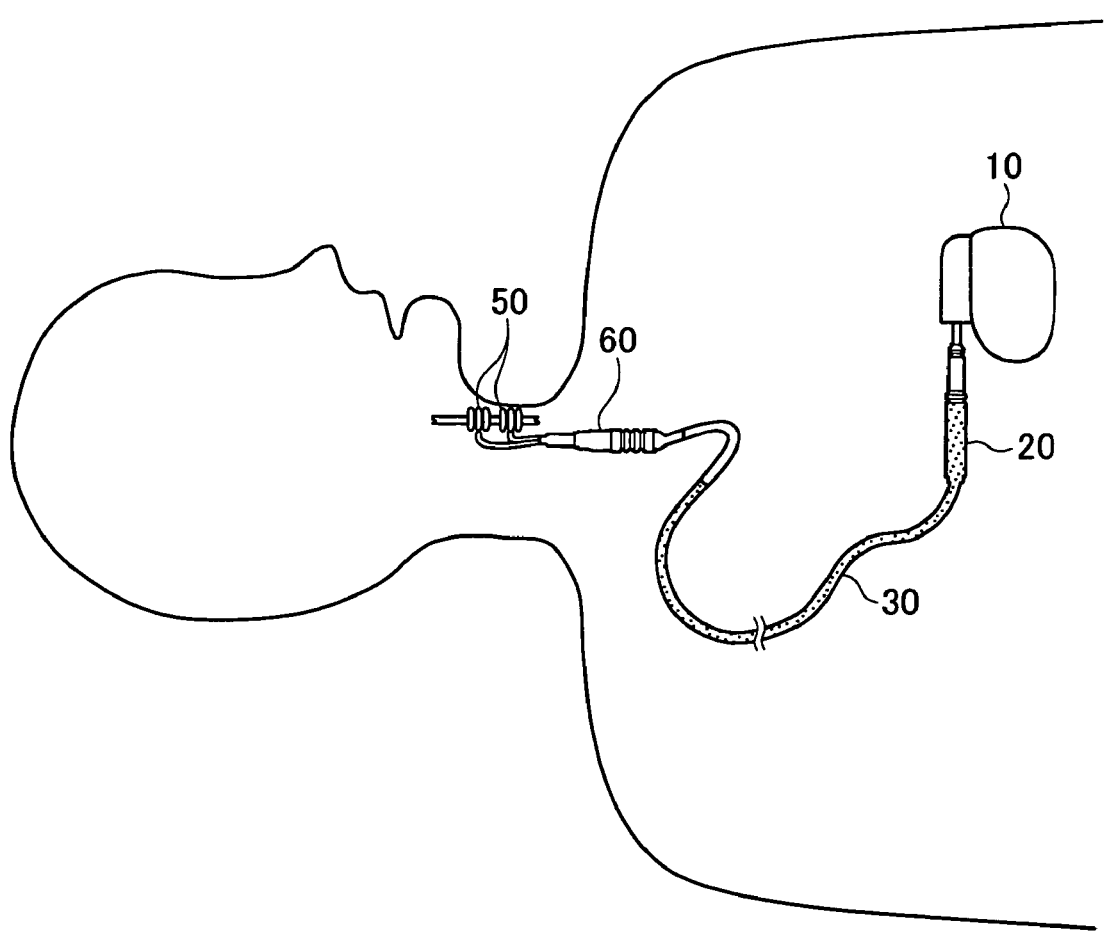
FIG. 5 is a schematic view showing the condition where the implantable electrode lead 1 has been installed in position.

FIG. 3 is a schematic view showing the condition before the implantable electrode lead 1 is passed through a subcutaneous tunnel (not shown), FIG. 4 is a general sectional view showing the manner in which the implantable electrode lead 1 is passed through the subcutaneous tunnel 62, and FIG. 5 is a schematic view showing the condition where the implantable electrode lead 1 has been installed in position.

First, as shown in FIG. 3, the electrode 50 of the implantable electrode lead 1 is fixed by winding it around the vagus nerve via an opening 67 formed by incising the cervical region, and the sutural sleeve (fixation portion 60) is fixed by suturing it to the muscle or subcutaneous tissue in the vicinity of the vagus nerve. Next, as shown in FIGS. 3 and 4, a subcutaneous tunnel 62 is formed by use of a pair of forceps 61, the pair of forceps 61 is inserted via an opening 66 on one side of the subcutaneous tunnel 62, the connector 20 or a portion near the connector 20 of the implantable electrode lead 1 inserted via the opening 67 in the cervical region is pinched by the pair of forceps 61, and is pulled in the direction of the opening 66, to be passed through the subcutaneous tunnel 62. In this case, since the conductor portion 30 of the implantable electrode lead 1 is provided on its surface with the lubricant coating layer 40 over a specified distance starting at the connector 20, the conductor portion 30 can be smoothly passed through the subcutaneous tunnel 62. Next, the connector 20 drawn to the opening 66 is connected to a nerve stimulator (implantable stimulation generator 10) implanted in a pocket beneath the skin of the left chest region via the opening 66, whereby the installation is completed.

Since the lubricant coating layer 40 is absent on the surface of the conductor portion 30 ranging at least from the base end of the fixation portion 60 to the electrode 50, when the implantable electrode lead 1 is strongly pulled, for example, after the installation of the implantable electrode lead 1 in the living body, the sutural sleeve would not slide on the surface of the conductor portion 30 and the electrode 50 is prevented from moving from the vagus nerve.

As has been described above, in the case where the electrode is connected to the vagus nerve and the connector is connected to the nerve stimulator implanted in the chest region, it is preferable that the whole length of the implantable electrode lead is 400 to 500 mm, the lubricant coating layer is provided on the surface of the conductor portion over a distance of not less than 100 mm from the connector, and the lubricant coating layer is absent on the surface of the conductor portion over a distance of not less than 30 mm from the electrode.

While the case of connecting the electrode to the vagus nerve has been taken as an example here, in other cases, for example, in the case where the electrode is connected to the spinal cord and the connector is connected to an implantable stimulation generator implanted in the lumbar region, it is preferable that the whole length of the implantable electrode lead is 300 to 600 mm, the lubricant coating layer is provided on the surface of the conductor portion over a distance of not less than 100 mm in the distal direction starting at the connector, and the lubricant coating layer is absent on the surface of the conductor portion over a distance of not less than 30 mm in the proximal direction starting at the electrode.

In the above-described implantable electrode lead, the lubricant coating layer is provided on the surface of the conductor portion over a specified distance from the proximal portion of the implantable electrode lead, and the lubricant coating layer is absent on the surface of the conductor portion over a specified distance from the distal end of the implantable electrode lead, whereby it is possible to reduce the frictional force generated between the conductor portion and the subcutaneous tissue, muscle or the inside wall of the lumen of the subcutaneous tunneling tool or the like, and to enhance operability, at the time of installing the implantable electrode lead into the living body or withdrawing the implantable electrode lead therefrom; further, it is possible to assuredly fix the electrode to the body tissue, after the installation. Furthermore, where a lubricant coating layer containing a steroid-based antiphlogistic and being high in biocompatibility is provided on the surface of the conductor portion, it is possible to lessen the inflammation reaction generated due to the implanting of the implantable electrode lead into the living body, and to reduce the burden exerted on the patient.

EXAMPLES

Now, the present invention will be described more in detail below by way of Examples, which are not limitative of the invention.

Example 1

A nerve stimulatory lead formed by coating a metallic wire of a nickel-cobalt alloy, MP35N, with a silicone to have an outside diameter of 1.9 mm and a whole length of 430 mm was used as the conductor portion. The surface of the lead over a distance of 300 mm from one end was subjected to coating by immersion in an aqueous 30% isopropanol solution containing 15 mg/ml of photo-labeled polyvinyl pyrrolidone and 35 mg/ml of photo-babeled polyacrylamide, followed by drying at room temperature for 30 min and irradiation with ultraviolet rays for 3 min, to activate the photo-reactive groups present in the polymers and to form covalent bonds to the surface of the lead. As a result, a lead in which a lubricant coating layer is provided over a distance of 300 mm from the one end and the lubricant coating layer is absent over a distance of 130 mm from the other end was obtained. The lead exhibited excellent lubricity when wetted with physiological saline or water.

Next, a connector 20 was attached to the end provided with the lubricant coating layer 40, of the lead, and a sutural sleeve (fixation portion 60) and an electrode 50 with a overall length of 20 mm from the end not provided with the lubricant coating layer 40, of the lead, were attached to the lead, to obtain an implantable electrode lead 1 shown in FIG. 1.

Subsequently, the implantable electrode lead 1 was inserted under the subcutaneous tissue.

FIG. 4 is a general sectional view showing the manner in which the implantable electrode lead 1 is passed through a subcutaneous tunnel 62. After the subcutaneous tunnel 62 was formed by use of a pair of forceps 61, the pair of forceps 61 was inserted via an opening 66 on one side of the subcutaneous tunnel 62, the connector 20 or the proximal portion 2 of the implantable electrode lead 1 inserted via an opening 67 on the other side was pinched with the pair of forceps 61, and was pulled in the direction of the opening 66, to be passed through the subcutaneous tunnel 62. In this case, the implantable electrode lead 1 could be smoothly inserted without being caught on the subcutaneous tissue 63 or muscle 65.

Figure 6:
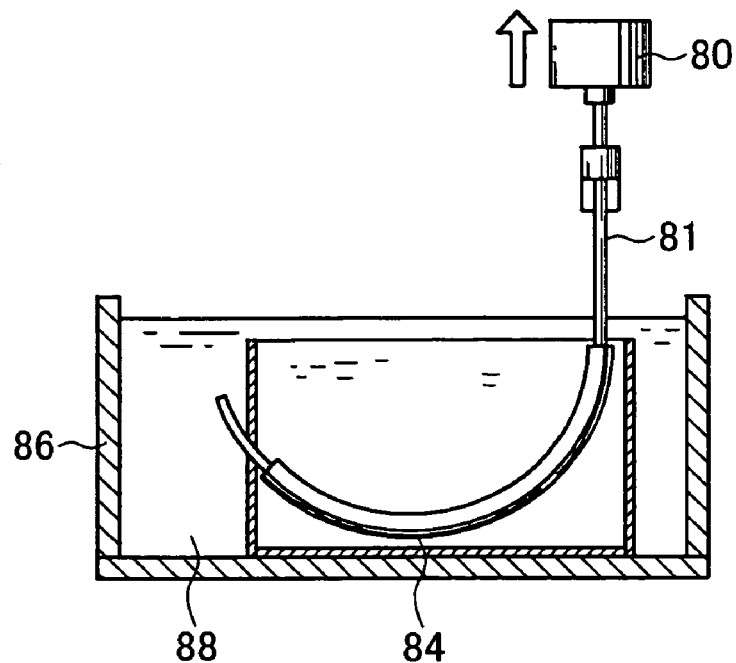
FIG. 6 is a schematic view of an experimental apparatus for evaluation of the lubricity of the implantable electrode lead 1.

FIG. 6 is a schematic view of an experimental apparatus for evaluation of the lubricity of the implantable electrode lead 1. As shown in FIG. 6, a test for evaluating the lubricity of the implantable electrode lead obtained in Example 1 was carried out. A lead specimen 81 provided thereon with a lubricant coating layer 40 over a distance of 300 mm from one end thereof in the same manner as the implantable electrode lead 1 was inserted into an ETFE tube 84 (inside diameter: 3.33 mm; length: 240 mm) fixed in a water tank 86 filled with water 88 in the state of being bent at a radius of 88 mm, one end of the specimen 81 was fixed to a load cell 80, and the maximum load at the time of drawing out the specimen 81 by 100 mm at a rate of 200 mm/min was measured. The measurement was conducted three times, and the average of the measured values is given in Table 1. In the table, SE means errors generated in the plurality of (three) times of test.

Figure 7:
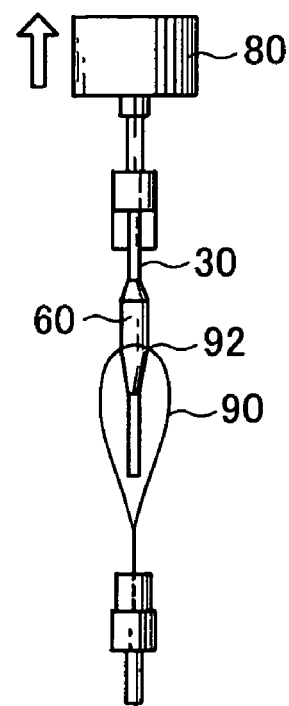
FIG. 7 is a schematic view of an experimental apparatus for measurement of a fixing force of a fixation portion 60 of the implantable electrode lead 1 to a conductor portion 30.

FIG. 7 is a schematic view of an experimental apparatus for measurement of the fixing force of the fixation portion 60 relative to the conductor portion 30 in the implantable electrode lead 1. As shown in FIG. 7, the fixing force of the fixation portion 60 relative to the conductor portion 30 was measured by use of the implantable electrode lead 1 in which the fixation portion 60 in Example 1 was located on the surface of the conductor portion 30 where the lubricant coating layer 40 is absent.

One end of the conductor portion 30 was fixed to a load cell 80, was ligatured from the outer periphery of a ligation portion of the fixation portion 60 with a force of 18 N by use of a suture 90, and was immersed in physiological saline at 37° C. for 10 days. Thereafter, the conductor portion 30 and the suture 90 were pulled by holding them respectively, and the load at the time when the fixation portion 60 was moved on the conductor portion 30 was measured. The test was carried out three times, and the average of the measured values was given in Table 2.

Comparative Example 1

An implantable electrode lead was produced by using the same lead (outside diameter: 1.9 mm; whole length: 430 mm) as that in Example 1 and without providing a lubricant coating layer on the surface of the lead (conductor portion).

Then, insertion under the subcutaneous tissue was carried out in the same manner as in Example 1. In this case, the implantable electrode lead was caught on the subcutaneous tissue 63 or the muscle 65, and the insertion was difficult to carry out.

A test for evaluating the lubricity of the implantable electrode lead in Comparative Example 1 was conducted by the same method as in Example 1. The test was conducted three times. The result is given in Table 1.

TABLE 1

| | Lubricant coating layer | Draw-out resistance (average ± SE) |
|---|---|---|
| Example 1 | Present | 0.02 ± 0.00 (N) |
| Comparative Example 1 | absent | 3.55 ± 0.29 (N) |

Comparative Example 2

An implantable electrode lead provided thereon with a lubricant coating layer 40 over the whole length of the lead (conductor portion) was produced by using the same lead (outside diameter: 1.9 mm; whole length: 430 mm) and the same method as in Example 1.

Then, insertion under the subcutaneous tissue was conducted in the same manner as in Example 1. In this case, the implantable electrode lead was not caught on the subcutaneous tissue 63 or the muscle 63, and could be inserted smoothly.

By use of the implantable electrode lead in which the fixation portion 60 was located on the surface of the conductor portion 30 where the lubricant coating layer 40 was provided according to Comparative Example 2, the fixing force of the fixation portion 60 relative to the conductor portion 30 was measured by the same method as in Example 1. The test was carried out three times. The result is shown in Table 2.

TABLE 2

| | Lubricant coating layer | Fixing force (average ± SE) |
|---|---|---|
| Example 1 | absent | 4.71 ± 0.71 (N) |
| Comparative Example 2 | present | 2.83 ± 0.29 (N) |

From Table 1 it is clear that the lead not provided with the lubricant coating layer in Comparative Example 1 showed a large draw-out resistance, which shows that the frictional force generated between the lead and inside wall of the ETFE tube was large. On the other hand, the lead in Example 1 showed little resistance, which shows that there was little frictional force generated between the lead and the inside wall of the ETFE tube, so that the lead can be smoothly inserted into a living body.

From Table 2 it is seen that the lead in which the fixation portion was provided on the conductor provided thereon with the lubricant coating layer in Comparative Example 2 showed a small fixing force, which shows that the fixation portion would be easily slid on the conductor. On the other hand, the lead in which the fixation portion was provided on the conductor portion where the lubricant coating layer was absent in Example 1 showed a large fixing force, so that the fixation portion would not slide on the conductor, and the implantable electrode lead can be assuredly fixed in a living body.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. An implantable electrode lead comprising:
   a distal portion having at least one electrode;
   a proximal portion having a connector for connection to an implantable stimulation generator which is disposed in a living body and comprises a power source for said electrode;
   a conductor portion which is connected to said distal portion and said proximal portion and is composed of an electrical conductor for transmission of electrical signals and an insulator covering the outside of said electrical conductor; and
   a fixation portion having a tip end and a base end for disposing over a portion of said conductor portion, wherein
   a lubricant coating layer is provided on a part of the surface of said conductor portion, and
   said lubricant coating layer is absent on the conductor portion surface ranging at least from the portion disposed at said base end of said fixation portion to the portion provided with said electrode, of the surface of said conductor portion.

2. An implantable electrode lead as set forth in claim 1, wherein the material constituting said lubricant coating layer is a hydrophilic polymeric material developing lubricity when wetted.

3. An implantable electrode lead as set forth in claim 2, wherein said hydrophilic polymeric material is polyvinyl pyrrolidone (PVP) or an acrylic acid-based polymer.

4. An implantable electrode lead as set forth in claim 3, wherein said hydrophilic polymeric material further contains a steroid-based antiphlogistic or is covalent-bonded to a steroid-based antiphlogistic.

5. An implantable electrode lead as set forth in claim 1, wherein the components have such sizes that said electrode can be disposed at a cervical nerve of said living body and said connector can be disposed in the chest region of said living body, at the time of implanting.

6. An implantable electrode lead comprising:
   a distal portion having at least one electrode;
   a proximal portion having a connector for connection to an implantable stimulation generator which comprises a power source for said electrode and is disposed in a living body; and
   a conductor portion which is connected to said distal portion and said proximal portion and is composed of an electrical conductor for transmission of electrical signals and an insulator covering the outside of said electrical conductor, wherein
   a lubricant coating layer is provided on the surface of said conductor portion over a distance of not less than 100 mm in the distal direction starting at said connector, and
   said lubricant coating layer is absent on the surface of said conductor portion over a distance of not less than 30 mm in the proximal direction starting at said electrode.

7. An implantable electrode lead as set forth in claim 6, wherein the material constituting the lubricant coating layer is a hydrophilic polymeric material.

8. An implantable electrode lead as set forth in claim 7, wherein said hydrophilic polymeric material is polyvinyl pyrrolidone (PVD) or an acrylic acid-based polymer.

9. An implantable electrode lead as set forth in claim 8, wherein said hydrophilic polymeric material further contains a steroid-based antiphlogistic or is covalent-bonded to a steroid-based antiphlogistic.

10. An implantable electrode lead as set forth in claim 6, wherein the components have such sizes that said electrode can be disposed at a cervical nerve of said living body and said connector can be disposed in the chest region of said living body, at the time of implanting.

* * * * *